United States Patent [19]
Tyms et al.

[11] Patent Number: 5,939,430
[45] Date of Patent: Aug. 17, 1999

[54] COMBINATIONS OF RETROVIRAL INHIBITORS

[75] Inventors: A. Stanley Tyms; Debra L. Taylor, both of London, United Kingdom

[73] Assignee: Merrell Pharmaceuticals Inc., Bridgewater, N.J.

[21] Appl. No.: 08/492,089

[22] PCT Filed: Jan. 18, 1994

[86] PCT No.: PCT/US94/00710

§ 371 Date: Jul. 20, 1995

§ 102(e) Date: Jul. 20, 1995

[87] PCT Pub. No.: WO94/19008

PCT Pub. Date: Sep. 1, 1994

[30] Foreign Application Priority Data

Feb. 22, 1993 [GB] United Kingdom .................. 9303518

[51] Int. Cl.$^6$ .................. A61K 31/44; A61K 31/16; A61K 31/36; A61K 31/35; A61K 31/47
[52] U.S. Cl. .................. 514/299; 514/451; 514/464; 514/616; 514/307
[58] Field of Search .................. 514/307, 299, 514/451, 464, 616

[56] References Cited

U.S. PATENT DOCUMENTS

| | | | |
|---|---|---|---|
| 5,036,101 | 7/1991 | Hsu et al. | 514/423 |
| 5,041,438 | 8/1991 | Hsu | 514/221 |
| 5,141,735 | 8/1992 | Bellemin et al. | 424/85.1 |
| 5,157,041 | 10/1992 | Handa et al. | 514/314 |

FOREIGN PATENT DOCUMENTS

| | | | |
|---|---|---|---|
| 0309952 | 9/1988 | European Pat. Off. | A61K 31/435 |
| 0309952 | 4/1989 | European Pat. Off. | A61K 31/435 |
| 0346847 | 12/1989 | European Pat. Off. | C07D 267/16 |
| 0432694 | 6/1991 | European Pat. Off. | C07D 217/26 |
| 0432695 | 6/1991 | European Pat. Off. | A61K 31/47 |
| 0475231 | 3/1992 | European Pat. Off. | A61K 31/55 |
| 0491218 | 6/1992 | European Pat. Off. | C07D 43/04 |
| 9212123 | 7/1992 | European Pat. Off. | A61K 31/395 |
| 0503203 | 9/1992 | European Pat. Off. | A61K 37/64 |
| 9212123 | 7/1992 | WIPO | A61K 31/325 |

OTHER PUBLICATIONS

Katob, et al., Nature, vol. 399, pp. 654–656 (1987).
Taylor, et al., Antiviral Research 10:11–26 (1988).
Taylor, et al., AIDS 5(6):693–698 (1991), Current Sciences Ltd., ISSN 0269–9370.
Wills, et al., AIDS 5(6):639–654 (1991), Current Sciences Ltd., ISSN 0269–9370.
Roberts, et al., Science, vol. 248:358–361 (Apr. 20, 1990).
McQuade, et al., Science, vol. 247:454–456 (Jan. 26, 1990).
Meek, et al., Nature, vol. 343:90–92 (Jan. 4, 1990).
Ashorn, et al., Proc. Natl. Acad. Sci. USA 87:7472–7476 (1990).
Roberts, et al., Biochem. Soc. Trans., 20(2):513–16 (1992).
Sachs, Arch. Intern. Med., 152(3):485–501 (1992).
Derwent Abstract CA 116(17):165807v (Holmes, et al., Antiviral Chem., 2(5):287–93 (1991) has been ordered and will be sent later).

*Primary Examiner*—Russell Travers
*Attorney, Agent, or Firm*—T. Helen Payne

[57] ABSTRACT

The combination of compounds of formula I and II can be used for the treatment of retroviral infections. The combination can be used to treat AIDS and ARC and other diseases caused by the retrovirus HTV or other related viruses.

28 Claims, No Drawings

COMBINATIONS OF RETROVIRAL INHIBITORS

This application is a 371 of PCT/US94/00710.

This invention relates to novel combinations of castanospermine esters and short peptide analogs that act effectively in their combination in the treatment of retroviral infections, particularly in the treatment of acquired immune deficiency syndrome (AIDS) and related human immunodeficiency viral (HIV) infections.

BACKGROUND OF THE INVENTION

Intense research over the last several years has been devoted to develop treatments and cures for retroviral viral infections in humans and in animals, and particularly for acquired immune deficiency syndrome (AIDS) and AIDS related complex (ARC). Today the public realizes the severe health risk posed by the AIDS retrovirus and that the incidence of ARC and AIDS in humans is increasing at an alarming rate. Furthermore, survival beyond 5 years for those who have contracted AIDS remains remote. Further, AIDS patients whose immune systems have been seriously impaired by the infection, suffer from numerous opportunistic infections and proliferative disease including *Pneumocystis carninii* pneumonia and Kaposi's sarcoma. No cure for AIDS is known and current treatments are largely without adequate proof of efficacy and have numerous untoward side effects. Due to the severity of the disease, and with death the resultant outcome from the disease, fear of AIDS has resulted in social ostracism and discrimination against those having or suspected of having the disease.

The AIDS virus belongs to a general class of viruses known as retroviruses. As a class, many of the known retroviruses are also oncogenic or tumor causing. Indeed the first two human retroviruses discovered, denoted human T-cell leukemia virus type I and type II or HTLV-I and II, were found to cause rare leukemias in humans after infection of T-lymphocytes. The third such human virus to be discovered, HTLV-III, now referred to as HIV, was found to cause cell death after infection of T-lymphocytes and has been identified as the causative agent of acquired immune deficiency syndrome (AIDS) and AIDS related complex (ARC).

Retroviruses are a class of ribonucleic acid (RNA) containing viruses that replicate by using a reverse transcriptase activity to form a strand of complementary DNA (cDNA) from which a double stranded, proviral DNA is produced. This proviral DNA is then incorporated into the chromosomal DNA of the host cell making possible viral replication by transcription of this integrated DNA and translation of viral messenger RNA into proteins. Replication of the virus occurs by synthesis of viral genomic RNA and its assembly with glycosytated and non-glycosylated viral proteins to form new viral particles. Maturation of virions at the cell surface results in the release of infectious virus progeny.

Retroviral proteins are generally synthesized as polyproteins and virus encoded proteases are required to cleave the precursor polyproteins to form the viral enzymes and structural proteins. For example, the gag and gag-pol precursor polyproteins of retroviruses are synthesized as precursors of viral encoded enzymes and non-glycosylated structural proteins. Similarly, the envelope protein of HTV is a 160 kDa highly glycosylated precursor glycoprotein. The envelope proteins are cleaved by a host-cell protease to give a 120 kDa external glycoprotein (gp 120) and a transmembrane glycoprotein (gp 41). The gp 120 protein contains a high affinity binding site that recognizes the CD4 ligand on CD4-positive human T-helper cells, the known receptor for this virus.

The retroviral proteases also show certain commonality by their inhibition by aspartyl protease-specific inhibitors, Iyoko, et al. Nature 329, 654–67. Similarly, amino acid sequencing of the retroviral proteases show they possess sequence homology. Because of their mutual structural and functional characteristics and their obligate function, the aspartyl proteases serve as a potentially interesting therapeutic target for intervention.

The correctly processed envelope glycoproteins of the retroviruses play an important role in the virus life cycle, which also offers a possible target for clinical intervention. The envelope glycoproteins serve a role in both the initial interaction of the virion and the target host-cell and in the subsequent fusion of the viral envelope and host-cell membranes during penetration. Certain esters of castanospermine are useful in interfering with the processing of the viral envelope glycoproteins and thereby in preventing the initial virus-host cell interaction and subsequent fusion.

The applicants have discovered that the combination of aspartyl protease-specific inhibitors (formula II) with glycoprotein processing inhibitors such as castanospermine derivatives (formula I) result in significant improvements in the inhibition of the HIV virus that would not be expected.

SUMMARY OF THE INVENTION

The pharmaceutical compositions consist of the glucosidase inhibitor of formula I and a viral aspartyl protease inhibitor of formula II.

The pharmaceutical compositions of formula 1 and formula II, and their pharmaceutically acceptable addition salts, are novel and possess valuable pharmacological properties. Often these compositions can act synergistically to effectively inhibit HIV activities, and therefore, can be used in the prophylaxis or treatment of viral infections, particularly infections caused by HIV.

Objects of the present invention are the compositions of formula I and II, and their aforementioned salts, for use as therapeutically active substances, medicaments containing said compounds and salts, their manufacture, and the use of said compositions and salts in the control or prevention of illnesses, especially in the treatment or prophylaxis of HIV infections.

Compounds of formula I comprise structures of the following formula:

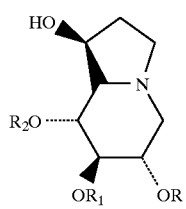

(1)

wherein R, $R_1$ and $R_2$ are independently hydrogen, $C_{1-14}$ alkanoyl, $C_1$–$C_{14}$ alkenoyl, cyclohexanecarbonyl, $C_{1-6}$ alkoxyacetyl,

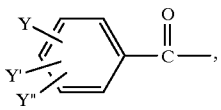

naphthalenecarbonyl optionally substituted by methyl or halogen; phenyl($C_{2-6}$ alkanoyl) wherein the phenyl is optionally substituted by methyl or halogen; cinnamoyl; pyridinecarbonyl optionally substituted by methyl or halogen; dihydropyridine carbonyl optionally substituted by $C_{1-10}$ alkyl; thiophenecarbonyl optionally substituted by methyl or halogen; or furancarbonyl optionally substituted by methyl or halogen; Y is hydrogen, $C_{1-4}$ alkyl, $C_{14}$ alkoxy, halogen, trifluoromethyl, $C_{1-4}$ alkylsulfonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; with R, $R_1$ and $R_2$ being selected in such a way that at least one of them, but not more than two of them, is hydrogen; or a pharmaceutically acceptable salt of these compounds.

The $C_{1-14}$ alkanoyl groups referred to above can be straight- or branched-chain or cyclic and can be exemplified by formyl, acetyl, propionyl, butyryl, isobutyryl, cyclopropanecarbonyl, hexanoyl, octanoyl and decanoyl. The $C_{1-14}$ alkenoyl groups referred to above can be straight- or branched-chain or cyclic but have at least one carbon-carbon double bond as exemplified, propenoyl, butenoyl, isobutenoyl, hexenoyl, octenoyl and decenoyl. The $C_{1-6}$ alkoxyacetyl referred to above can be methoxy-acetyl, ethoxyacetyl and butoxyacetyl. The halogens referred to above can be exemplified by fluorine, chlorine, bromine or iodine. The $C_{2-6}$ alkanoyl groups referred to above can be exemplified by acetyl, propionyl, butyryl, isobutyryl, and hexanoyl. The $C_{1-4}$ alkyl groups referred to above, whether alone or as part of an alkoxy, an alkylsulfonyl or an alkylmercapto group, can be straight- or branched-chain alkyl groups containing up to 4 carbon atoms. Examples of various such groups are methyl, ethyl, propyl, butyl, methoxy, ethoxy, butoxy, methylsulfonyl, ethylsulfonyl, methylmercapto and ethylmercapto. The phenyl($C_{2-6}$ alkanoyl) groups referred to above can be exemplified by benzeneacetyl and benzenepropionyl. The various naphthalenecarbonyl, pyridinecarbonyl, thiophenecarbonyl and furancarbonyl groups referred to above include the various position isomers and these can be exemplified by naphthalene-1-carbonyl, naphthalene-2-carbonyl, nicotinoyl, isonicotinoyl, N-methyl-dihydro-pyridine-3-carbonyl, thiophene-2-carbonyl, thiophene-3-carbonyl, furan-2-carbonyl and furan-3-carbonyl. The naphthalene, pyridine, thiophene and furan groups can be optionally further substituted as indicated above.

Preferred compounds of the present invention are those wherein R, $R_1$ and $R_2$ are 1 or 2 alkanoyl, alkenoyl, or benzoyl groups with the benzoyl substituted by Y, Y' and Y" as described above, especially a $C_{1-4}$ alkanoyl or a benzoyl optionally substituted with an alkyl or halogen.

More preferred are those compounds of formula 1 wherein one of R, $R_1$ and $R_2$ is alkanoyl or benzoyl, especially a $C_{1-8}$ alkanoyl, $C_{1-8}$ alkenoyl, or a benzoyl optionally substituted with an alkyl or halogen, and the others are hydrogens. Even more preferred are those compounds of formula 1 wherein one of R, $R_1$ and $R_2$ is a $C_{18}$ alkanoyl, $C_{1-8}$ alkenoyl, or a benzoyl optionally substituted with an alkyl or halogen, especially a methyl, bromo, chloro, or fluoro group, and the others are hydrogens.

Most preferred grouping are those compounds of formula 1 wherein $R_1$ is a $C_{1-8}$ alkanoyl, $C_{1-8}$ alkenoyl, or benzoyl optionally substituted with an alkyl or halogen, especially a methyl, bromo, chloro, or fluoro group, most especially a methyl, bromo, chloro, or fluoro group at the para position, and wherein R and $R_2$ are each a hydrogen.

A most especially preferred grouping can be designated by the substituents represented by the following compounds:

1. [1S-(1α,6β,7α,8β,8aβ)]-octahydro-1,6,7,8-indolizinetetrol 6-benzoate:
2. [1S-(1α,6β,7α,8β,8aβ)]-octahydro-1,6,7,8-indolizinetetrol 7-benzoate:
3. [1S-(1α,6β,7α,8β,8aβ)]-octahydro-1,6,7,8-indolizinetetrol 6-(4-methylbenzoate):
4. [1S-(1α,6β,7α,8β,8aβ)]-octahydro-1,6,7,8-indolizinetetrol 7-(4-bromobenzoate):
5. [1S-(1α,6β,7α,8β,8aβ)]-octahydro-1,6,7,8-indolizinetetrol 6,8-dibutanoate:
6. A castanospermine ester of claim 1 which is [1S-(1α,6β,7α,8β,8aβ)]-octahydro-1,6,7,8-indolizinetetrol 6-butanoate:
7. [1S-(1α,6β,7α,8β,8aβ)]-octahydro-1,6,7,8-indolizinetetrol 6-(2-furancarboxylate):
8. [1S-(1α,6β,7α,8β,8aβ)]-octahydro-1,6,7,8-indolizinetetrol 7-(2,4-dichlorobenzoate)
9. [1S-(1α,6β,7α,8β,8aβ)]-octahydro-1,6,7,8-indolizinetetrol 6-(3-hexenoate).
10. [1S-(1α,6β,7α,8β,8aβ)]-octahydro-1,6,7,8-indolizinetetrol 6-octanoate.
11. [1S-(1α,6β,7α,8β,8aβ)]-octahydro-1,6,7,8-indolizinetetrol 6-pentanoate.

Certain compounds are preferred. Amongst the preferred compounds of formula I is [1S-(1α,6β,7α,8β,8aβ)]-octahydro-1,6,7,8-indolizinetetrol 6-butanoate.

Preparation, and preferred grouping of compounds of compounds of formula I are also taught in the U.S. Pat. No. 5,017,563, Issued May 21, 1991, which is herein incorporated by reference. Processes for the preparation of Castanospermine are also taught in U.S. Pat. No. 5,066,807, Issued Nov. 19, 1991, which is herein incorporated by reference.

Compound of the formula II comprise structures of the following formula:

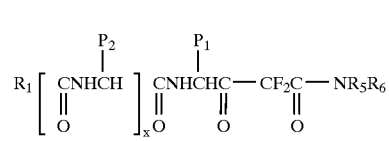

II and the hydrates, isosteres and the pharmaceutically acceptable salts thereof wherein x is zero or one, r $P_1$ is Q, or B, B being

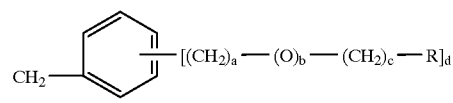

with the proviso that B is other than p-hydroxy-benzyl or p-alkoxybenzyl, a is zero, or 1, 2 or 3, b is zero or 1, c is zero or 1, 2, 3, 4 or 5,
d is 1 or 2,
e is zero, 1 or 2,
Q is

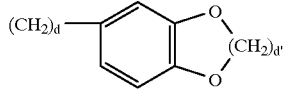

$P_2$ is $C_{1-6}$ alkyl, cyclopentyl, cyclohexyl, hydroxy $C_{1-6}$ alkylene,,

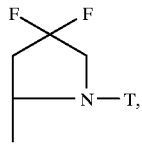

with T being H or $C(O)R_4$, $CH_2CONHR4$, or $CH_2CONHR4$;
R is hydrogen, —$CH_2CHO$, hydroxy $C_{1-6}$ alkylene, $C_{1-6}$ alkoxy $C_{1-6}$alkylene, $C_{1-6}$ alkyl, phenyl,

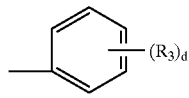

or Q,
$R_1$ is benzyloxy, $C_{1-6}$ alkoxy, $C_{1-6}$ alkyl, phenyl, benzyl, phenethyl, fluorenylmethylenoxy, 2-isoquinolinyl, PDL,

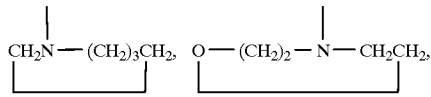

$NHSO_2R_4$, $N(R_4)$(benzyl), and $N(R_4)$(PDL), with PDL being —$(CH_2)_a$-2-,3-, or 4-pyridyl, or p-W-substituted benzyloxy with W being nitro, OH amino, $C_{1-6}$ alkoxy, or hydroxy $C_{1-6}$ alkylene, or halogeno,
$R_3$ is $C_{1-6}$ allenyl $C_{1-6}$ alkoxy, $C_{1-6}$ alkoxy $C_{1-6}$ alkylene, hydroxy $C_{1-6}$ alkylene, $C_{1-6}$ alkyl, H, or OH,
$R_4$ is H, $C_{1-6}$ alkyl, phenyl or benzyl,
$R_5$ is H, $C_{1-6}$ alkyl, OH, $C_{1-6}$ alkoxy,

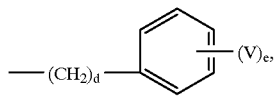

V being $OR_4$ or hydroxy $C_{1-6}$ alkylene, $CH_2Si(CH_3)_2(R_3)$, —$(CH_2)_d$—Q, PDL,

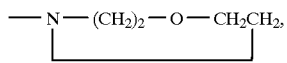

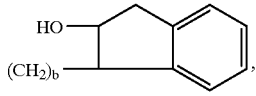

-continued

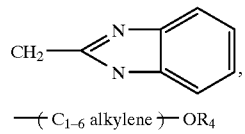

or —CH(Y)(Z), Y being hydroxy $C_{1-6}$ alkylene, $C_{1-6}$ alkyl, or $(CH_2)_e$—$C_6H_4$—$(V)_e$, and Z being CHO, $CO_2R_4$, $CO_2NHR_4$ or $(CH_2)_e$—$OR_4$,
$R_6$ is as defined for $R_5$ with the proviso that $R_6$ is other than H when $R_5$ is H, and when $R_5$ and $R_6$ are taken together with nitrogen atom to which they are attached form a heterocyclic moiety of the formulae:

(a)
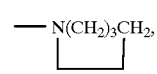

(b)
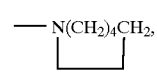

(c)
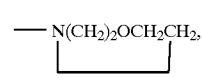

(d)
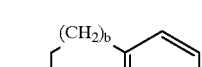

(e)
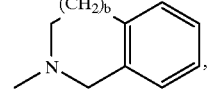

(f)
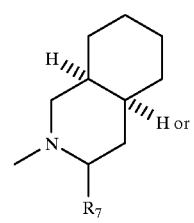

(g)
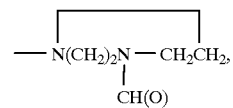

(h)
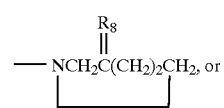

(i)
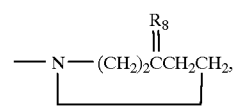

$R_7$ is $CH_2OR_4$ or $C(O)NHR_4$,
$R_8$ is (H,OH) or =O.

As is true for most classes of compounds found to be useful in the pharmaceutical industry, certain subgeneric groups and certain specific compounds are more preferred. Within the concepts of this invention, it is to be found that the preferred compounds are those wherein when $R_5$ is H, then:

$R_1$ is benzyl, benzyloxy, 4-alkoxybenzyloxy, morpholyl,

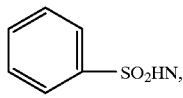

(3-pyridyl)ethyl, isoquinolyl;
  $P_2$ is methylamid, isopropyl, cyclopentyl, 2-(4,4-difluoro)-pyrrolidyl, 2-hydroxy-2-propyl, t-butyl;
  $P_1$ is piperonyl, 4-(benzyloxy)benzyl, 3-(benzyloxy)benzyl, (4-benzyloxy-3-methoxy)benzyl;
  $R_6$ is benzyl, piperonyl, $CH_2$-pyridyl, 4-(benzyloxy)benzyl, morpholino, tetrahydroisoquinolyl, 4-(3-hydroxypropyl)benzyl,
2-(3-hydroxypropyl)benzyl, and

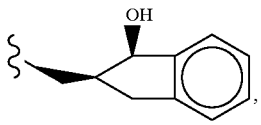

or —CH(Y)(Z) with Y and Z both being as generally defined, but particularly when Y is isopropyl, preferably in the D configuration, or phenyl and when Z is benzyloxymethylene, CHO, COOH, alkoxy or $COOR_4$.

When $R_5$ is other than H it is preferred that $R_5$ be methyl, 4-hydroxybutyl or 3-hydroxypropyl and that $R_6$ be benzoxy or benzyl, and when $R_5$ and $R_6$ form a heterocyclic moiety with the nitrogen attached thereto, the heterocycle is a perhydroisoquinoline of (f),

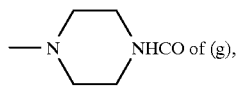

and morpholino of (c) be the heterocyclic moieties. The preferred specific compounds of formula II are those shown in the chart below and those products exemplified herein.

A most especially preferred grouping can be designated by the substituents represented by the following compounds:
1. N-tertiary butyl-decahydro-2 [2(R)-hydroxy-4-phenyl-3(S)-[[N(2-quinolylcarbonyl)-L-asparaginyl]amino]-butyl]-(4aS,8aS)-isoquinoline-3-(S)-carboxamide.
2. [1(S)-[[3,3-difluoro-2,4,-dioxo-1-[[4-(phenylmethoxy)phenyl]methyl]-4-[(phenylmethyl)amino]butyl]aminocarbonyl]-2-methylpropyl]carbamic acid, phenylmethyl ester.
3. N-[4-(N-benzyloxycarbonyl-L-valyl)amino-2,2-difluro-1,3,-dioxo-5-(4-benzyloxy)phenyl-pentyl](O-benzyl)-D-valinol.

The specific making and compounds of compounds of formula II are further taught in the International Application Published Under the Patent Cooperation Treaty, International Publication Number WO 92/12123, herein incorporated by reference.

In the present invention, each compound in the compositions compounds of formula I and II may occur with asymmetric centers or may occur as racemates, racemic mixtures and as individual diastereomers, with all isomeric forms of the compounds being included in the present invention.

The preferred compounds of formula I and formula II may be selected in any combination from one group select from formula I and one group selected from formula II. It is recognized that such combinations would include, for instance, a pharmaceutical composition comprising a compound of formula I:

Formula I

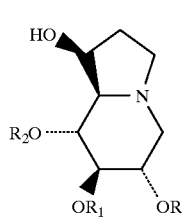

wherein $R_1$ is a $C_{1-8}$ alkanoyl, $C_{1-10}$ alkenoyl, $C_{1-8}$ alkoxyacetyl, or benzoyl optionally substituted with an alkyl or halogen group; or a pharmaceutically acceptable salt thereof and a compound of formula II Formula II

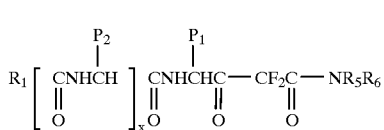

and the hydrates, isosteres and the pharmaceutically acceptable salts thereof wherein $R_1$ is benzyl oxy,

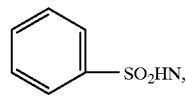

(3-pyridyl)ethyl, isoquinolyl, 4-alkoxybenzyloxy, or morpholyl, $P_2$ is isopropyl, cyclopentyl, 2-(4,4-difluoro)-pyrrolidyl, 2-hydroxy-2-propyl, t-butyl, $P_1$ is piperonyl, 4-(benzyloxy)benzyl, 3-(benzyloxy)benzyl, (4-benzyloxy-3-methoxy)benzyl, when $R_5$ is H, $R_6$ is benzyl, piperonyl, $CH_2$-pyridyl, 4-(benzyloxy)benzyl, morpholino, tetrahydroisoquinolyl, 4-(3-hydroxypropyl)benzyl, 2-(3-hydroxypropyl)benzyl, and

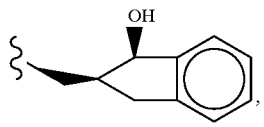

or —CH(Y)(Z) with Y and Z both being as generally defined, but particularly when Y is isopropyl, preferably in the D configuration, or phenyl and when Z is benzyloxymethylene, CHO, COOH, alkoxy or $COOR_4$, when $R_5$ is other than H it is preferred that $R_5$ be methyl, 4-hydroxybutyl or 3-hydroxypropyl and that $R_6$ be benzoxy or benzyl, and when $R_5$ and $R_6$ form a heterocyclic moiety with the nitrogen attached thereto, it is preferred that

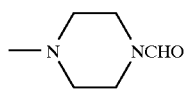

and morpholino be the heterocyclic moieties. It is further understood further subgroupings from the above combination may be made from the groups of formula I and II defined herein.

| R₁ | P₂ | P₁ | R₅ = H, R₆ |
| --- | --- | --- | --- |
| benzyloxy | isopropyl | piperonyl | benzyl |
| benzyloxy | isopropyl | piperonyl | piperonyl |
| ⌬–SO₂NH | isopropyl | 4-(benzyloxy)benzyl | benzyl |
| benzyloxy | isopropyl | 3-(benzyloxy)benzyl | benzyl |
| benzyloxy | t-butyl | 3-(benzyloxy)benzyl | benzyl |
| benzyloxy | isopropyl | (4-benzyloxy-3-methoxy)benzyl | benzyl |
| benzyloxy | isopropyl | (4-benzyloxy-3-methoxy)benzyl | piperonyl |
| benzyloxy | 2-hydroxy-2-propyl | 4-(benzyloxy)benzyl | benzyl |
| (3-pyridyl)ethyl | isopropyl | 4-(benzyloxy)benzyl | —CH₂—(3-pyridyl) |
| isoquinolyl | isopropyl | 4-(benzyloxy)benzyl | —CH₂—(3-pyridyl) |
| (3-pyrdiyl)ethyl | isopropyl | 4-(benzyloxy)benzyl | —C₂H₅—(2-pyridyl) |
| (3-pyridyl)ethyl | isopropyl | 4-(benzyloxy)benzyl | —CH₂—(2-pyridyl) |
| benzyloxy | t-butyl | 4-(benzyloxy)benzyl | isobutyl-CH₂-O-benzyl (D) |
| benzyloxy | isopropyl | 4-(benzyloxy)benzyl | CH(Ph)CHO |
| (3-pyridyl)ethyl | isopropyl | 4-(benzyloxy)benzyl | CH(Ph)CHO |
| isoquinolyl | isopropyl | 4-(benzyloxy)benzyl | isobutyl-CH₂-OCH₃ (D) |
| benzyloxy | isopropyl | 4-(benzyloxy)benzyl | isobutyl-CH₂-OCH₃ (D) |

-continued

| | | | |
|---|---|---|---|
| benzyloxy | isopropyl | 4-(benzyloxy)benzyl | 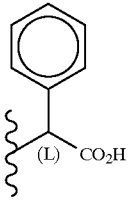 |
| benzyloxy | isopropyl | 4-(benzyloxy)benzyl | 4-(benzyloxy)benzyl |
| benzyloxy | t-butyl | 4-(benzyloxy)benzyl | 4-(benzyloxy)benzyl |
| (3-pyridyl)ethyl | isopropyl | 4-(benzyloxy)benzyl | 4-(benzyloxy)benzyl |
| benzyloxy | isopropyl | 4-(benzyloxy)benzyl | 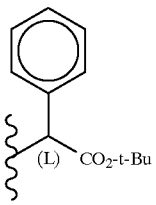 |
| benzyloxy | isopropyl | 4-(benzyloxy)benzyl | 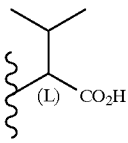 |
| 4-O-methyl-benzyloxy | isopropyl | 4-(benzyloxy)benzyl | benzyl |
| benzyloxy | isopropyl | 4-(benzyloxy)benzyl | 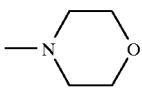 |
| benzyloxy | isopropyl | 4-(benzyloxy)benzyl | 4-(3-hydroxy-propyl)benzyl |
| benzyloxy | isopropyl | 4-(benzyloxy)benzyl | 2-(3-hydroxy-propyl)benzyl |
| benzyloxy | isopropyl | 4-(benzyloxy)benzyl | 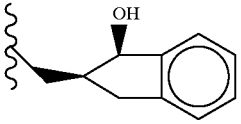 |

| $R_1$ | $P_2$ | $P_1$ | $R_5, R_6$ |
|---|---|---|---|
| benzyloxy | isopropyl | 4-(benzyloxy)benzyl | $R_5 = CH_3$, $R_6 =$  |
| (3-pyridyl)ethyl | isopropyl | 4-(benzyloxy)benzyl | $R_5 = CH_3$, $R_6 =$ benzyl |
| (3-pyridyl)ethyl | cyclopentyl | 4-(benzyloxy)benzyl | $R_5 = CH_3$, $R_6 =$ benzyl |
| benzyloxy | 2-(4,4-difluoro) pyrrolidyl | 4-(benzyloxy)benzyl | $R_5 = CH_3$, $R_6 =$ benzyl |
| morpholyl | isopropyl | 4-(benzyloxy)benzyl | $R_5 = CH_3$, $R_6 =$ benzyl |
| (3-pyridyl)ethyl | isopropyl | 4-(benzyloxy)benzyl | $R_5 =$ 4-hydroxypropyl $R_6 =$ benzyl |
| benzyloxy | isopropyl | 4-(benzyloxy)benzyl | $R_5 =$ 4-hydroxypropyl $R_6 =$ benzyl |
| (3-pyridyl)ethyl | isopropyl | 4-(benzyloxy)benzyl | $R_5, R_6 =$ morpholyl |
| (3-pyridyl)ethyl | cyclopentyl | 4-(benzyloxy)benzyl | $R_5, R_6 =$ morpholyl |
| benzyloxy | isopropyl | 4-(benzyloxy)benzyl | $R_5, R_6 =$ 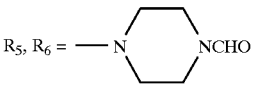 |
| (3-pyridyl)ethyl | isopropyl | 4-(benzyloxy)benzyl | tetrahydro- |

| benzyl | methylamide | benzyl | isoquinolyl perhydroiso-quinoline-CONHt-Bu |

DETAILED DESCRIPTION OF THE INVENTION

The pharmaceutical compositions of the present invention are useful as inhibitors of retroviral proteases and cellular γ-glucosidase I which are required for virus replication, particularly HIV-1 and HIV-2, the prevention or treatment of infection by the human immunodeficiency virus (HIV), and the treatment of consequent pathological conditions such as the acquired immunodeficiency syndrome (AIDS) in mammals capable of being infected with HIV virus. Treating AIDS (preventing infection by HIV or treating infection by HIV) is defined as including, but not limited to, treating a wide range of states of HIV infection: AIDS, ARC (AIDS related complex), both symptomatic and asymptomatic, and actual or potential exposure to HIV. For example, the pharmaceutical compositions of this invention are useful in preventing infection by HIV after suspected past exposure to HIV by, e.g., blood transfusion, accidental needle stick, or exposure to patient blood during surgery.

For these purposes, the compounds of the present invention may be administered orally, parenterally (including subcutaneous injections, intravenous, intramuscular, transdermal, intrasternal injection or infusion techniques), by inhalation spray, or rectally, in dosage unit formulations containing convention non-toxic pharmaceutically acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compounds of formula I and II of the present invention, or a pharmaceutically acceptable salt thereof.

These pharmaceutical compositions may be in the form of orally-administerable suspensions or tablets; nasal sprays; sterile injectable preparations, for example, as sterile injectable aqueous or oleagenous suspensions or suppositories) or they may be administered transdermally.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweetener/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

For oral administration the compositions of formula 1 can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

When administered by nasal aerosol or inhalation, these compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solublizing or dispersing agents known in the art.

The compositions including formula 1 and 2 may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidize and/or dissolve in the rectal cavity to release the drug.

The pharmaceutically acceptable addition salts, either cation or anion salts, are those salts that are not substantially toxic at the dosage administered to achieve the desired effect and do not independently possess significant pharmacological activity. The conversion of the composition of formula I and II may independently or jointly be formulated as addition salts. Illustratively, cation salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabiethylamine, N-(lower)alkylpiperidine, and any other suitable amine. Sodium salts are preferred. An acceptable acid addition salt may be carried out by treating such compounds in a conventional manner with an inorganic acid or example a hydrobromic acid, sulfphuric acid, nitric acid, phosphoric acid etc., or with an organic acid such as acetic acid, citric acid, maleic acid, fumaric acid, tartaric acid, methanesulfonic acid, p-toluenesulphonic acid.

Dosage levels of the order of 0.02 to 5.0 or 10.0 grams per day of the composition are useful in the treatment or prevention of the above-indicated conditions, with oral doses two to five times higher. For example, infection by HIV is effectively treated by the administration of from 10 to 50 milligrams of the compound per kilogram of body weight from one to three times per day. It will be understood, however, that the specific dose level and frequency of dosage for any particular patient may be varied and will depend upon a variety of factors including the activity of the specific compounds employed, the metabolic stability and length of action of compounds in combination with each other, the age, body weight, general health, sex, diet, mode and time of administration, rate of excretion, drug combination the severity of the particular condition, and the host undergoing therapy.

The present invention is also directed to combinations of the HIV protease-inhibitory compounds with one or more agents useful in the treatment of AIDS, such as, for example, with known antiviral agents suitable for treating HIV 1 and HIV 2 viral infections, e.g., a ester of castanospermine of formula I with a viral protease inhibitor of formula II. For instance, the present invention includes the use of a glycoprotein processing inhibitor of formula I and a aspartyl protease specific inhibitor of formula II and for the preparation of a pharmaceutical formulation for simultaneous, separate or sequential use for treating an HIV infection wherein the said compounds of formula 1 are

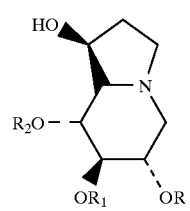

Formula I wherein $R_1$ is a $C_{1-8}$ alkanoyl, $C_{1-10}$ alkenoyl, $C_{1-8}$ alkoxyacetyl, or benzoyl optionally substituted with an alkyl or halogen group; or a pharmaceutically acceptable salt thereof and said compound of formula II is

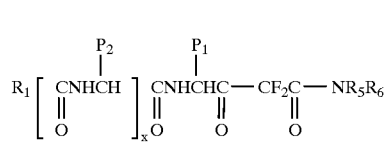

Formula II and the hydrates, isosteres and the pharmaceutically acceptable salts thereof wherein $R_1$ is benzyl oxy,

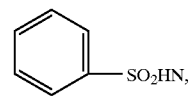

(3-pyridyl)ethyl, isoquinolyl, 4-alkoxybenzyloxy, or morpholyl, $P_2$ is isopropyl, cyclopentyl, 2-(4,4-difluoro)-pyrrolidyl, 2-hydroxy-2-propyl, t-butyl, $P_1$ is piperonyl, 4-(benzyloxy)benzyl, 3-(benzyloxy)benzyl, (4-benzyloxy-3-methoxy)benzyl, when $R_5$ is H, $R_6$ is benzyl, piperonyl, $CH_2$-pyridyl, 4-(benzyloxy)benzyl, morpholino, tetrahydroisoquinolyl, 4-(3-hydroxypropyl)benzyl, 2-(3-hydroxypropyl)benzyl, and

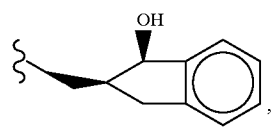

or —CH(Y)(Z) with Y and Z both being as generally defined, but particularly when Y is isopropyl, preferably in the D configuration, or phenyl and when Z is benzyloxymethylene, CHO, COOH, alkoxy or $COOR_4$, when $R_5$ is other than H it is preferred that $R_5$ be methyl, 4-hydroxybutyl or 3-hydroxypropyl and that $R_6$ be benzoxy or benzyl, and when $R_5$ and $R_6$ form a heterocyclic moiety with the nitrogen attached thereto, it is preferred that

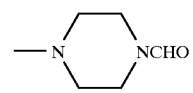

and morpholino be the heterocyclic moieties. It is further understood further subgroupings from the above combination may be made from the groups of formula I and II defined herein.

A preferred composition containing the compounds of formula I and II are those compositions which contain at least 10% of the compounds of formula I or those compositions that contain at least 10% of the compounds of formula II.

The compounds of this invention may be assayed for their inhibition of HIV replication using the following published techniques.

EXPERIMENTAL PROCEDURES

The following examples illustrate various aspects of this invention. The following information on reagents, cell lines, virus strains and assays describe the usefulness of the previously described compositions. Further methods and procedures dealing with the assays are known in the art.

To study the effects of the described compositions the growth of HIV-1 was used to study the treatment of AIDS as a useful model for HIV.

Drug Combination Assay

For the investigation of drug combinations, the MTT cell viability assay (Pauwels et al., J. Virol. Methods, 1988, 20, 309–321) was used. Various drug combinations were achieved by creating chequerboards with one compound being titrated horizontally with the second compound being titrated vertically across a 96 well microtitre plate using multichannel pipettes. The use of six microtiter plates was required for each assay (only inner 60 wells) with quadruplicate wells for each drug combination. Doubling dilutions or half log dilutions, with the end rows left drug free, were usually made.

MT-4 cells infected with 100 TCID$_{50}$ of HIV-LRF per $5\times10^4$ cells were added to each well at a concentration of $5\times10^4$ cells per well and after incubation at 37° C. of six days, 10 μl of acidified isopropanol was added and the plates read at 540nm using a Multiscan MCC/340 spectrophotometer (Flow Laboratories). The raw plate data were captured onto floppy discusing Ultroterm (LKB). Subsequent data reduction was performed using Excel (Microsoft). This enabled the mean O.D. values for each drug combination to be calculated and a series of 19 dose response curves, i.e. the dose response of each drug at a fixed concentration of the other to be generated with minimal user intervention. The top four left hand corner wells which received the highest concentration of each drug were used as a positive control (i.e. cells viable totally protected) and the four bottom right hand corner wells without any drug were used as the negative control (i.e. total cell death).

Analysis of Drug Combinations by Isobolic Method

From the dose response curves, the IC50 for each drug, either alone or in combination with a fixed concentration of the other, was calculated and isobolograms plotted (Suhnel, Antiviral Research 13, 23–40(1990)). It was possible to determine from the shape of the isobole whether the drugs had a synergistic relationship (concave), additive effect (linear) or showed anatagonism (convex). Additionally a combination index (CI) was calculated (Suhnel, 1990).

The table provides ED50 values computed from dose response lines for each compound in the presence of a fixed concentration of the other compound.

From these data was determined the combination index (CI) from the formula:

$$CI = \frac{(D)_1}{(DX)_1} + \frac{(D)_2}{(DX)_2} + \frac{\alpha(D)_1(D)_2}{(Dx)_1(Dx)_2}$$

where α=1 for mutually non-exclusive agents
and (DX)$_1$=IC 50 of drug 1 above;
(DX)$_2$=IC 50 of drug 2 above;

(D)1 and (D)2 =concentrations of drugs 1 and 2 in combination giving 50% inhibition;

If it is:
<1 (synergism);
CI=1 (zero interaction);
>1 (antagonism).
(ref: J. Suhnel, Antiviral Research 13 (1990), 23–40.)

EXAMPLE 1

ANTIVIRAL ACTIVITY OF RO-31-8959 AND MDL7369 WITH BUCAST

Three protease inhibitors MDL73669 (Tables 1A and 1B), Ro-31-8959 (Tables 2A and 2B) and MDL 74538 (Tables 3A and 3B) were investigate in combination with the glycoprotein processing inhibitor MDL 28574 (BUCAST). The method used to test the effectiveness of the combination was assessed by looking at the various concentrations of the compounds in combination on antiviral activity determined by using the cell viability assay previously described. The method of study of these compounds allowed for identification of synergistic interactions by analysis of the data values for a Combination Index (C.I.).

The following abbreviations apply to the following compounds:

MDL73669=[1(S)-[[3,3-difluoro-2,4,-dioxo-1-[[4-(phenylmethoxy)phenyl]methyl]-4-[(phenylmethyl)amino]butyl]aminocarbonyl]-2-methylpropyl) carbamic acid, phenylmethyl ester.

MDL74538=N-[4-(N-benzyloxycarbonyl-L-valyl)amino-2,2-difluoro-1,3,-dioxo-5-(4-benzyloxy)phenylpentyl]-(O-benzyl)-D-valinol.

MDL28574=(Bucast)[1S-(1α,6β,7α,8β,8aβ)]-octahydro-1,6,7,8-indolizinetetrol 6-butanoate Ro-31-8959=N-tertiary butyl-decahydro-2 [2(R)-hydroxy-4-phenyl-3(S)-[[N(2-quinolylcarbonyl)-L-asparaginyl]amino]-butyl]-(4aS,8aS)-isoquinoline-3 (S)-carboxamide.

Table 1A and 1B: Concentrations of MDL73669 and BMDL28574, in combination and alone required to give 50% protection of MT-4 cells infected with HIV-lRF and the combination indices calculated from these values.

| Fixed Conc MDL 73669 (μM) | IC 50 MDL 28574 (μM) | C.I.* |
|---|---|---|
| 0 | 100 | — |
| 0.0001 | 100 | — |
| 0.0003 | 100 | — |
| 0.001 | 45 | 0.45 |
| 0.003 | 25 | 0.25 |
| 0.010 | 21 | 0.22 |
| 0.03 | 32 | 0.37 |
| 0.1 | 20 | 0.4 |
| 0.3 | 30 | 0.95 |
| 1 | — | — |

*The combination (C.I.) indices indicate synergy

| Fixed Conc MDL 28574 (μM) | IC 50 MDL 73669 (μM) | C.I.* |
|---|---|---|
| 0 | 0.6 | — |
| 0.1 | 0.55 | — |

-continued

| Fixed Conc MDL 28574 ($\mu$M) | IC 50 MDL 73669 ($\mu$M) | C.I.* |
|---|---|---|
| 0.3 | 0.6 | — |
| 1 | 0.5 | 0.85 |
| 3 | 0.5 | 0.89 |
| 10 | 0.42 | 0.87 |
| 30 | 0.002 | 0.3 |
| 100 | — | — |
| 300 | — | — |

*The combination (C.I.) indices indicate synergy

Table 2A and 2B: Concentrations of Ro-31-8959 and MDL 28574, in combination and alone required to give 50% protection of MT-4 cells infected with HIV-1$_{RF}$ and the combination indices calculated from these values.

| Fixed Conc Ro-31-8959 (nM) | IC 50 MDL 28574 ($\mu$M) | C.I.* |
|---|---|---|
| 0 | 100 | — |
| 0.1 | 50 | 0.52 |
| 0.3 | 60 | 0.66 |
| 1 | 12 | 0.28 |
| 3 | 6.8 | 0.52 |
| 10 | — | — |
| 30 | — | — |
| 100 | — | — |

*The combination (C.I.) indices indicate synergy

| Fixed Conc MDL 28574 ($\mu$M) | IC 50 Ro-31-8959 (nM) | C.I* |
|---|---|---|
| 0 | 6.9 | — |
| 0.1 | 6.7 | — |
| 0.3 | 9.0 | — |
| 1 | 6.1 | — |
| 3 | 12 | — |
| 10 | 1.4 | 0.32 |
| 30 | 0.38 | 0.37 |
| 100 | — | — |
| 300 | — | — |

*The combination (C.I.) indices indicate synergy

Table 3A and 3B: Concentrations of 74538 and MDL 28574, in combination and alone required to give 50% protection of MT-4 cells infected with HIV-1$_{RF}$ and the combination indices calculated from these values.

| Fixed Conc MDL 74538 (nM) | IC 50 MDL 28574 ($\mu$M) | C.I.* |
|---|---|---|
| 0 | 23 | — |
| 0.1 | 20 | 0.87 |
| 0.3 | 9.5 | 0.42 |
| 1.0 | 25 | 1.1 |
| 3.0 | 8.2 | 0.43 |
| 10.0 | 6.2 | 0.39 |
| 30.0 | 3.0 | 0.48 |

*The combination (C.I.) indices indicate synergy

| Fixed Conc MDL 28574 ($\mu$M) | IC 50 MDL 74538 (nM) | C.I.* |
|---|---|---|
| 0 | 100 | — |
| 3.0 | 30 | 0.47 |
| 10.0 | 2 | 0.46 |

*The combination (C.I.) indices indicate synergy

What is claimed is:

1. A pharmaceutical composition, comprising a compound of formula I which is [1 S-(1α,6β,7α,8β,8αβ-octahydro-1,6,7,8-indolizinetetrol 6-butonate or a pharmaceutically acceptable salt thereof,
and a synergistic amount of a compound of formula II selected from N-tertiary butyl-decahydro-2 [2(R)-hydroxy-4-phenyl-3(S)-[[N(2-quinolylcarbonyl)-L-asparaginyl]-amino]-butyl]-(4aS,8aS)-isoquinoline-3-(S)-carboxamide, [1(S)-[[3,3-difluoro-2,4-dioxo-1-[[4-(phenylmethyl)amino]butyl]aminocarbonyl]-2-methylpropyl]carboamic acid, phenylmethyl ester, or
N-[4-(N-benzyloxycarbonyl-L-valyl)amino-2,2-difluoro-1,3-dioxo-5-(4-benyloxy)phenyl-pentyl](O-benzyl)-D-valinol,
or the hydrates, isosteres and pharmaceutically acceptable salts thereof, where the synergistic amount of a compound of formula II results in a combination index of less than 1.

2. The pharmaceutical composition according to claim 8, wherein the compound of formula II is
N-tertiary butyl-decahydro-2 [2(R)-hydroxy-4-phenyl-3(S)-[[N(2-quinolylcarbonyl)-L-asparaginyl]amino]-butyl]-(4aS,8aS)-isoquinoline-3-(S)-carboxamide,
or the hydrates, isosteres and pharmaceutically acceptable salts thereof.

3. The pharmaceutical composition according to claim 2, wherein the combination index is equal to or less than 0.66.

4. The pharmaceutical composition according to claim 3, wherein the combination index is equal to or less than 0.32.

5. The pharmaceutical composition according to claim 2, wherein the ratio of a compound of formula I to a compound of formula II is from about 1:0.00002 to about 1:0.00044.

6. The pharmaceutical composition according to claim 2, wherein the ratio is from about 1:0.00002 to about 1:0.0014.

7. The pharmaceutical composition according to claim 2, wherein the ratio is from about 1:0.00002 to about 1:0.00013.

8. The pharmaceutical composition according to claim 1, wherein the compound of formula II is
[1(S)-[[3,3-difluoro-2,4-dioxo-1-[[4-(phenylmethyl)amino]butyl]aminocarbonyl]-2-methylpropyl] carboamic acid, phenylmethyl ester,
or the hydrates, isosteres and pharmaceutically acceptable salts thereof.

9. The pharmaceutical composition according to claim 8, wherein the combination index is equal to or less than 0.95.

10. The pharmaceutical composition according to claim 8, wherein the combination index is equal to or less than 0.85.

11. The pharmaceutical composition according to claim 8, wherein the combination index is equal to or less than 0.45.

12. The pharmaceutical composition according to claim 8, wherein the combination index is equal to or less than 0.25.

13. The pharmaceutical composition according to claim 8, wherein the ratio of a compound of formula I to a compound of formula II is from about 1:0.0002 to about 1:0.005.

14. The pharmaceutical composition according to claim 8, wherein the ratio is from about 1:0.0002 to about 1:0.01.

15. The pharmaceutical composition according to claim 8, wherein the ratio is from about 1:0.067 to about 1:0.5.

16. The pharmaceutical composition according to claim 1, wherein the compound of formula II is N-[4-(N-benzyloxycarbonyl-L-valyl)amino-2,2-difluoro-1,3-dioxo-5-(4-benyloxy)phenylpentyl](O-benzyl)-D-valinol, or the hydrates, isosteres and pharmaceutically acceptable salts thereof.

17. The pharmaceutical composition according to claim 16, wherein the combination index is equal to or less than 0.87.

18. The pharmaceutical composition according to claim 16, wherein the combination index is equal to or less than 0.48.

19. The pharmaceutical composition according to claim 16, wherein the combination index is equal to or less than 0.42.

20. The pharmaceutical composition according to claim 16, wherein the combination index is equal to or less than 0.39.

21. The pharmaceutical composition according to claim 16, wherein the ratio of a compound of formula I to a compound of formula II is from about 1:0.00005 to about 1:0.01.

22. The pharmaceutical composition according to claim 16, wherein the ratio is from about 1:0.00005 to about 1:0.03.

23. The pharmaceutical composition according to claim 1, wherein the ratio is from about 1:0.0037 to about 1:0.01.

24. The pharmaceutical composition according to claim 1, wherein the ratio is from about 1:0.002 to about 1:0.01.

25. The pharmaceutical composition according to claim 1, which comprises at least 10% of the compound of formula II.

26. The pharmaceutical composition according to claim 1, which comprises at least 10% of the compound of formula I.

27. The pharmaceutical composition according to claim 1, adapted for parenteral administration.

28. The pharmaceutical composition according to claim 1, wherein the compound of formula I or formula are a physiological functional salt or other derivative thereof, in an acceptable pharmaceutical vehicle.

* * * * *